(12) United States Patent
Stasz et al.

(10) Patent No.: US 6,254,545 B1
(45) Date of Patent: Jul. 3, 2001

(54) PYRO/PIEZO SENSOR

(75) Inventors: Peter Stasz, St. Paul; Charles Bille, White Bear Lake; David Gust, Andover, all of MN (US)

(73) Assignee: Dymedix, Corp., Minneapolis, MN (US)

( * ) Notice: Subject to any disclaimer, the term of this patent is extended or adjusted under 35 U.S.C. 154(b) by 0 days.

(21) Appl. No.: 09/416,660

(22) Filed: Oct. 12, 1999

(51) Int. Cl.[7] .................................................. A61B 5/08
(52) U.S. Cl. ........................... 600/529; 600/537; 600/552
(58) Field of Search ........................... 600/372, 382–383, 600/529, 533–538, 549, 552, 555; 374/178, 183, 185

(56) References Cited

U.S. PATENT DOCUMENTS 5,311,875  5/1994  Stasz .
5,825,293  * 10/1998  Ahmed et al. ................... 600/529 X
5,853,005  * 12/1998  Scanlon ............................ 600/437 X
6,070,098  *  5/2000  Moore-Ede et al. ............. 600/300 X

* cited by examiner

*Primary Examiner*—Cary O'Connor
*Assistant Examiner*—Ryan Carter
(74) *Attorney, Agent, or Firm*—Nikolai, Mersereau & Dietz, P.A.

(57) ABSTRACT

A combination thermal and vibration sensor for use in sleep monitoring equipment comprises a thin film of a plastic exhibiting both pyroelectric and piezoelectric properties. By providing a layer of foam material totally covering one major surface of the plastic film layer, it is found that the thermal mass of the sensor is changed to the point where the pyroelectric signal can more readily be isolated from the piezoelectric signal using conventional signal processing techniques.

11 Claims, 7 Drawing Sheets

PYRO/PIEZO SENSOR

BACKGROUND OF THE INVENTION

I. Field of the Invention

This invention relates generally to electronic sensors for monitoring both temperature changes and sound using a single transducer, and more particularly to the construction of such sensors that more readily allows the temperature signal to be separated from the sound signal using conventional signal processing techniques (filtering).

II. Discussion of the Prior Art

In the Stasz U.S. Pat. No. 5,311,875, which is hereby incorporated by reference, there is described a system for electronically monitoring breathing patterns. The system described therein utilizes a plastic film exhibiting both pyroelectric and thermoelectric properties such as a polyvinylidene fluoride (PVDF) film. The film transducer has a conductive electrode on opposed major surfaces thereof and electrical wires connect the electrodes to an electronics module that is designed to separate the transducer output into two separate channels, one being for temperature and the other being for sound or vibration.

Our testing has shown that the signal proportional to temperature variation greatly exceeds that due to noise or vibration by a factor of about 150:1. The temperature-related signal also exhibits a substantially faster response time than the sound signal and is rich in frequency components in the 20 Hz to 50 Hz range. These facts result in a difficulty in preventing the thermal component of the transducer from crossing over into the sound channel, often leading to the occurrence of false positives when both sound signals and temperature signals are being simultaneously monitored.

The problem thus presents itself as to how one may effectively separate the signals when the frequency components of each signal overlap. Resorting to a signal processing approach has proven difficult.

We have found that by modifying the mechanical construction of the pyro/piezo transducer to increase its thermal mass, the effective rise time of the thermal signal is greatly reduced, while not seriously attenuating the sound/vibration-related signal amplitude. Decreasing the rise time of the thermal signal results in a shift of the frequency components thereof so as not to overlap with the frequency components in the sound channel. As such, conventional filtering steps can be performed to produce separate, isolated channels.

SUMMARY OF THE INVENTION

In accordance with the present invention, control over the thermal mass of the transducer described in the aforereferenced Stasz patent is achieved by affixing a layer of plastic foam material onto the transducer film on one surface thereof. Thus, in accordance with a preferred embodiment of the present invention, the combination thermal and vibration sensor may comprise a PVDF film of a predetermined shape configuration with first and second major surfaces. A thin layer of a conductive material is deposited upon the first and second major surfaces of the film and electrical leads are attached at one end to the electrodes. An outer moisture impervious layer is adhered to the electrode on one side of the film and a foam layer of a predetermined thickness and coextensive with the area of the PVDF film is bonded to the opposite major surface. The thickness of the foam layer is inversely related to the rise time of the thermal signal. Lowering the rise time of the thermal signal effectively shifts the frequency components comprising the thermal signal so as to no longer overlap with the predominant frequency components of the piezo or sound signal. Now, conventional filtering techniques can be used to separate the two channels.

DESCRIPTION OF THE DRAWINGS

The foregoing features, objects and advantages of the invention will be come apparent to those skilled in the art from the following detailed description of a preferred embodiment, especially when considered in conjunction with the accompanying drawings in which.

DESCRIPTION OF THE PREFERRED EMBODIMENT

Figure 1:
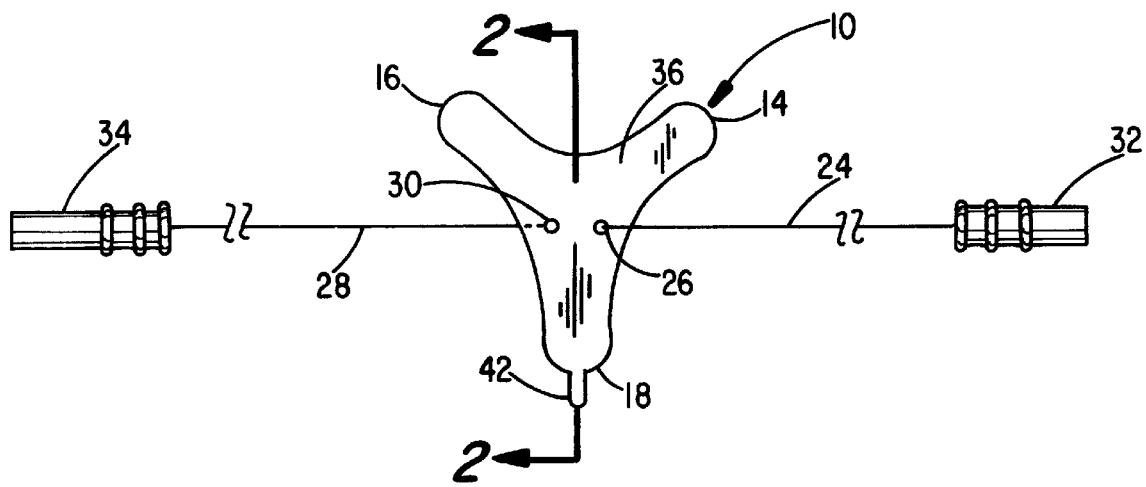
FIG. 1 is a front plan view of a pyro/piezo sensor constructed in accordance with the present invention.

Referring to FIG. 1, there is indicated generally by numeral 10 a transducer element constructed in accordance with the present invention. It comprises a laminated construction of a plastic film 12 which exhibits both pyroelectric and piezoelectric properties. A polyvinylidene fluoride (PVDF) whose thickness ranges from about 0.5 to 5 mils has proven suitable. The film 12 and the layers laminated therewith and yet to be described are preferably somewhat triangular in shape, but with the three sides of the triangle being arcuate (concave inward) to define three distinct lobes 14, 16 and 18.

Figure 2:
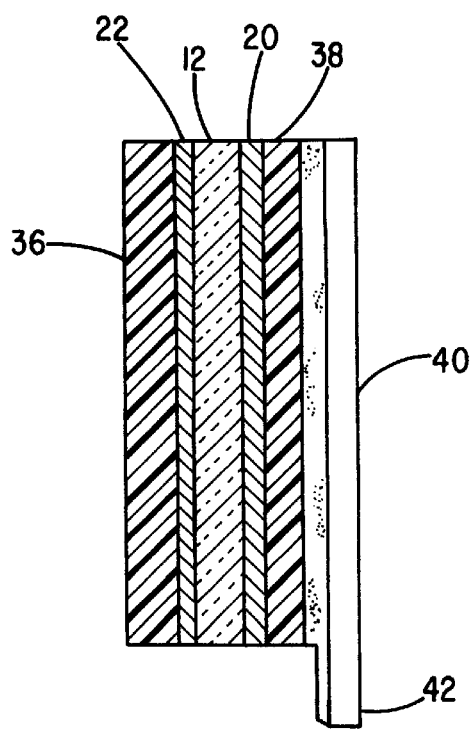
FIG. 2 is a side elevation view of the sensor of FIG. 1.

In fabricating the transducer, a thin, flexible layer of conductive material is applied to the opposed major surfaces of the film layer 12, the conductive layers being identified in FIG. 2 by numerals 20 and 22. Without limitation, the electrodes 20 and 22 may comprise carbon or a suitable metal that is sufficiently thin so as not to inhibit the bending and forming of the electrode during use.

As shown in FIG. 1, an elongated insulated conductor 24 has one end 26 thereof connected to the conductive layer 20 while elongated conductor 28 has one end 30 connected to the conductive layer 22 on the opposite side of film 12 from conductive layer 20. Conductors 24 and 28 are terminated in connectors 32 and 34, respectively, to facilitate their attachment to an electronics module (not shown).

Overlaying the conductive layer 22 is a non-conductive tape 36 which is shown as being coextensive with the film layer 12.

Adhered to the conductive layer 20 on the opposed surface of the film layer 12 is a layer 38. Either or both of the non-conductive layers 36 and 38 preferably may comprise a layer of plastic foam having a pressure sensitive adhesive on opposed surfaces thereof whereby the layers 36 and 38 adhere to the conductive layers 22 and 20, respectively. Assuming that the transducer is to be used in sleep-lab applications for monitoring a patient's breathing pattern, an adhesive on the exposed or outer surface of the foam layer 38 can be used to adhere the transducer to the subject's upper lip, with lobes 14 and 16 being positioned directly in the path of air flow from the subject's nares and with the lobe 18 adapted to overlay the subject's mouth opening. Prior to use, the adhesive is preferably protected by a peel-away layer of release paper, as at 40, the release paper having a pull-tab 42 extending beyond a border of the layer 38 for ease of gripping.

Figure 3:
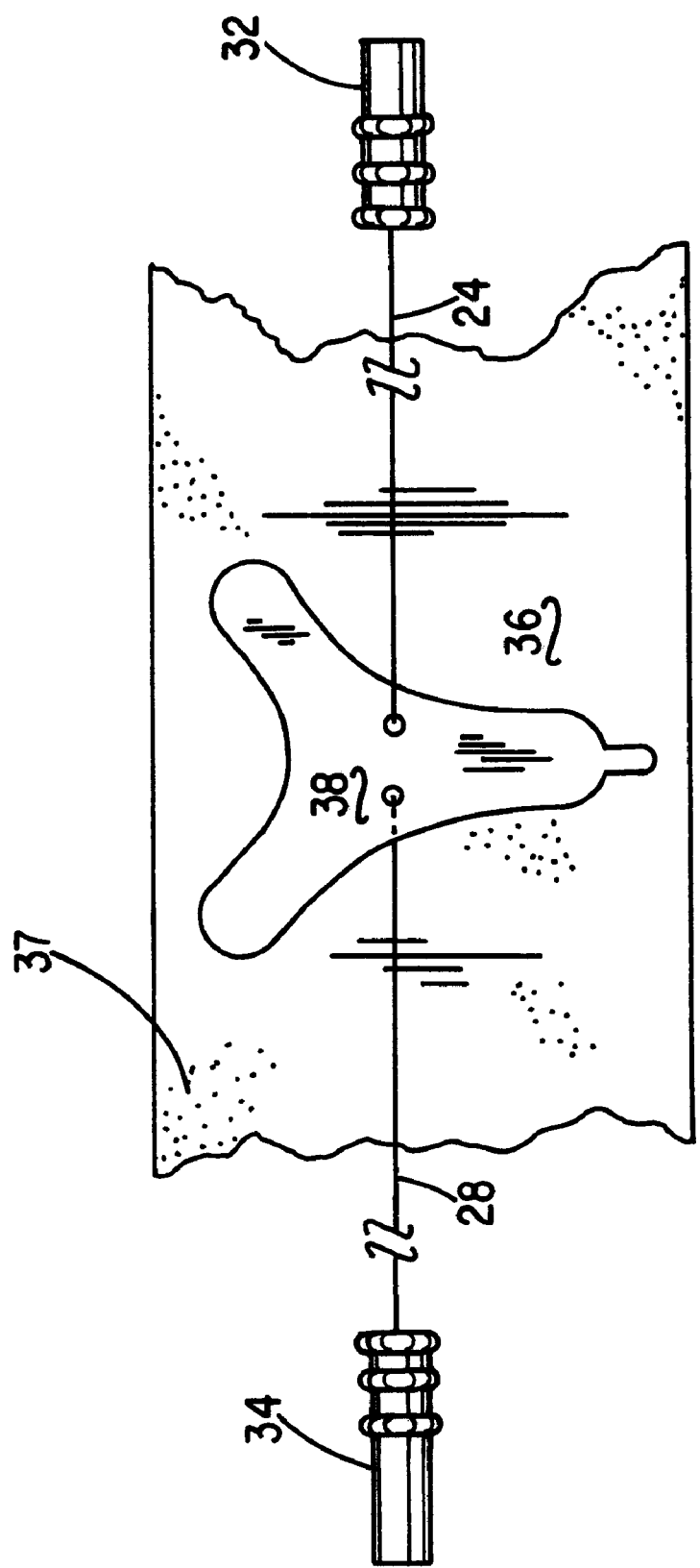
FIG. 3 is a plan rear view of an alternative embodiment.

Because the transducer made in accordance with the present invention is very flexible, it can adhere to the subject's lip and flex with facial movements so that it does not readily detach from the subject's lip. As shown in the embodiment of FIG. 3, the non-conductive tape layer 36 may not be co-extensive with the film layer, but instead may extend beyond the confines of the transducer film and may include a pressure sensitive adhesive on its undersurface 37 to facilitate attachment of the transducer to a subject being monitored. Again, the adhesive may be protected with a removable release paper to shield the adhesive prior to its application to the subject.

The present invention centers on the use of the covering layers 36 and/or 38 on the transducer described in the aforereferenced Stasz '875 patent. Specifically, we have found that it is possible to tailor the rise time of the thermal response signal component so that its frequency components do not overlap with the frequency components of the piezo (sound) signal. That is to say, the covering layers 36 and/or 38 are found to increase the thermal mass of the transducer to the point where the rise time of the thermal signal is reduced to a point where conventional filtering techniques can readily discriminate between the sound channel and the temperature channel as those terms are defined in the Stasz '875 patent. As such, transducers constructed in accordance with the present invention can be tailored to work with electronic signal processing circuitry currently in use in sleep labs, making it unnecessary to provide special electronics for accommodating combination pyro and piezo film transducers.

Figure 4A:
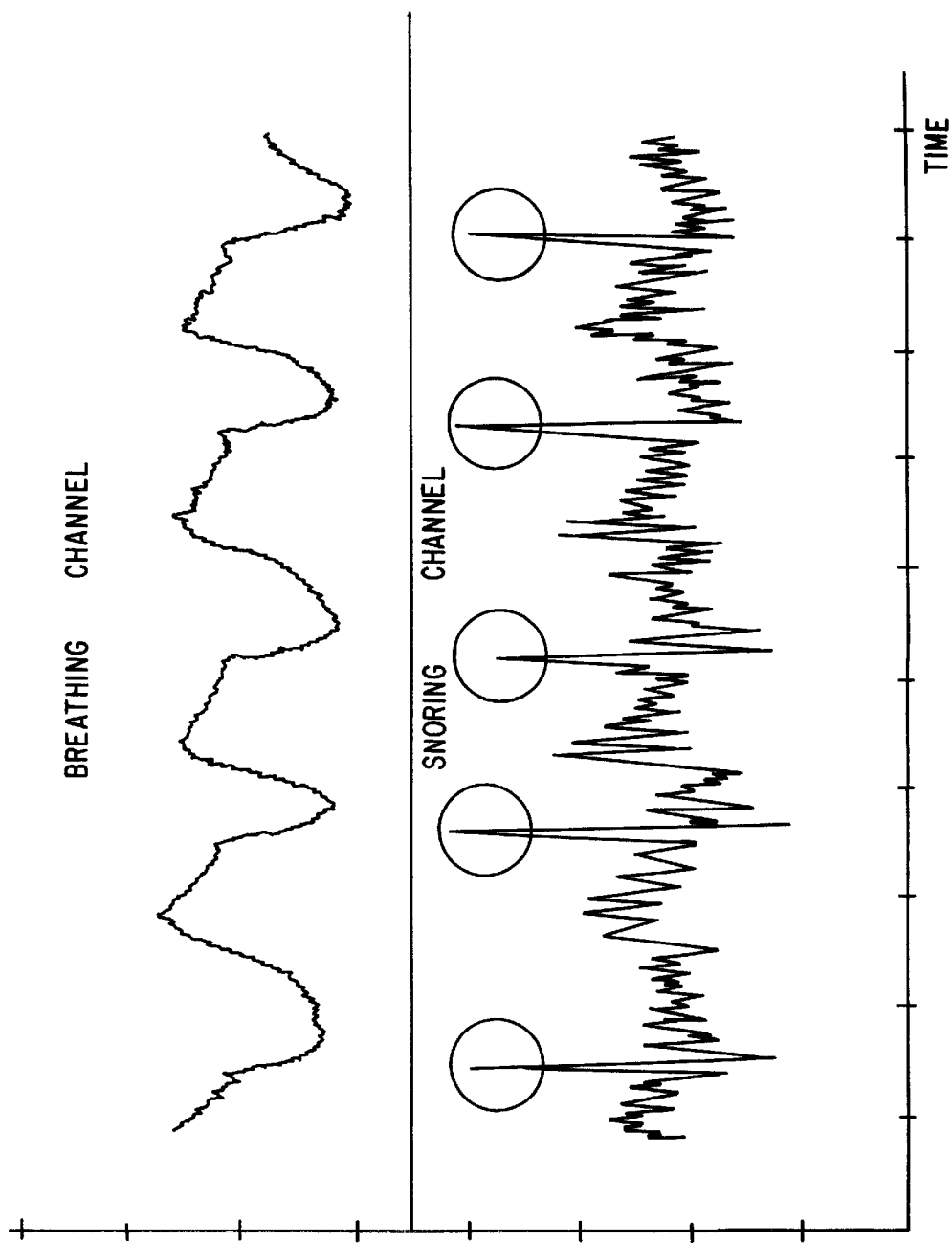
FIGS. 4A–4E are waveforms helpful in understanding the significance of the improvement afforded by the present invention.

FIG. 4A graphically illustrates how the signal from the prior art transducer described in the aforereferenced Stasz '875 patent frequently results in false positive in the snoring channel due to the rapid rise and fall time of the pyrosignal in the breathing channel. The false positives are highlighted by being encircled.

FIG. 4B again shows the behavior of the prior art transducer of the Stasz '875 patent in the presence of a snoring event. The breathing channel shows rhythmic breathing with an episode of snoring bounded by vertical dashed lines. Observing the waveform in the snoring channel, it is again noted that there are several false positives corresponding to the rapid fall time of the pyrosignal.

Figure 4B:
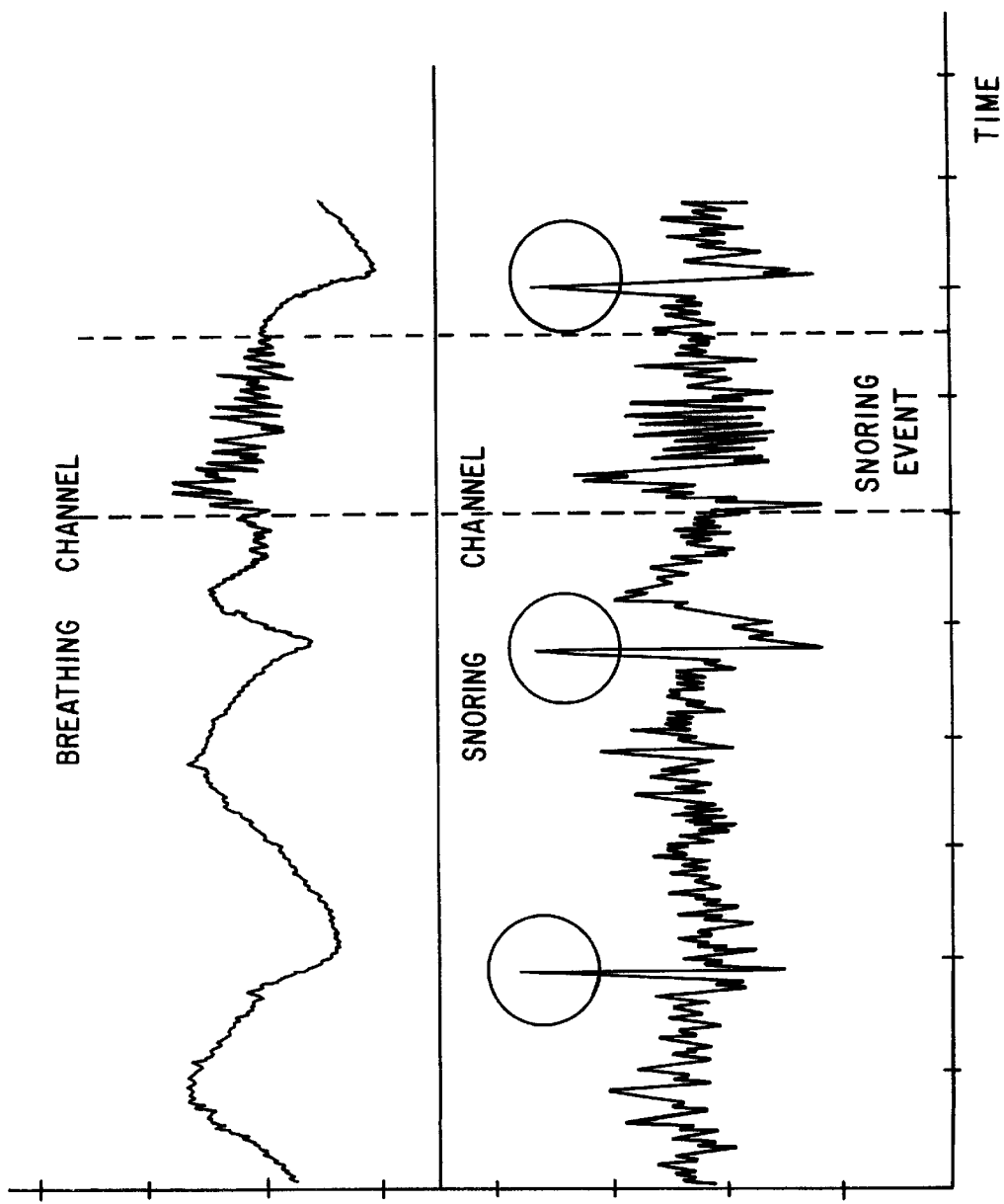
Figure 4C:
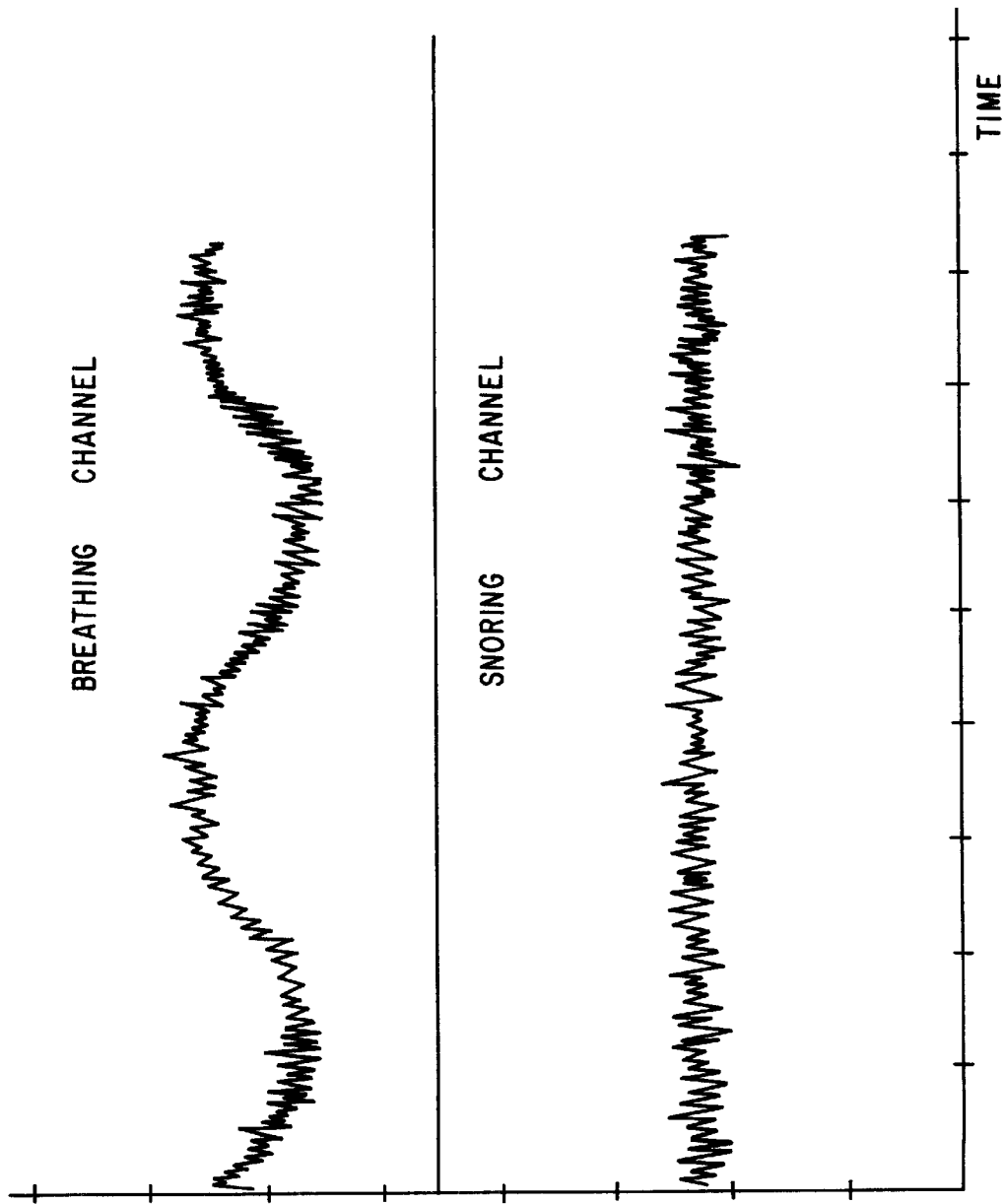

FIG. 4C illustrates the waveforms in the breathing and snoring channel when the transducer constructed in accordance with the present is employed with the same sensing circuitry as was used in recording the waveforms of FIGS. 4A and 4B. Looking first at the waveform in the breathing channel in FIG. 4C, it is immediately apparent that the addition of the foam layer covering the entire transducer film has the effect of significantly decreasing the rise and fall time of the pyro signal. As a result, there are no longer any false positive peaks in the waveformn derived from the snoring channel electronics.

Figure 4D:
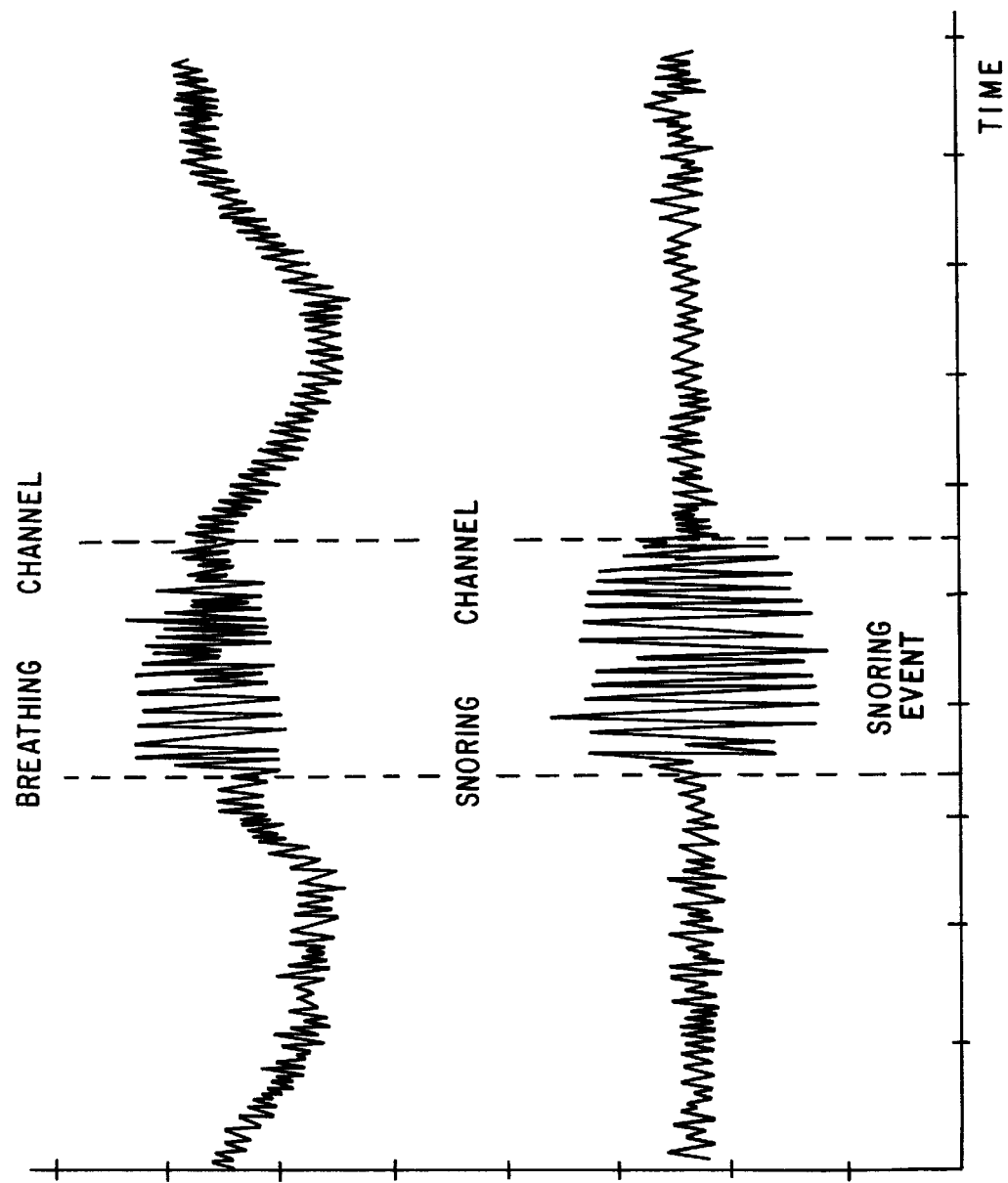

The waveform of FIG. 4D were taken using the transducer of the present invention but with a snoring episode taking place. Because of the absence of false positives, the output from the snoring or piezo channel is readily recognized and detectable.

Figure 4E:
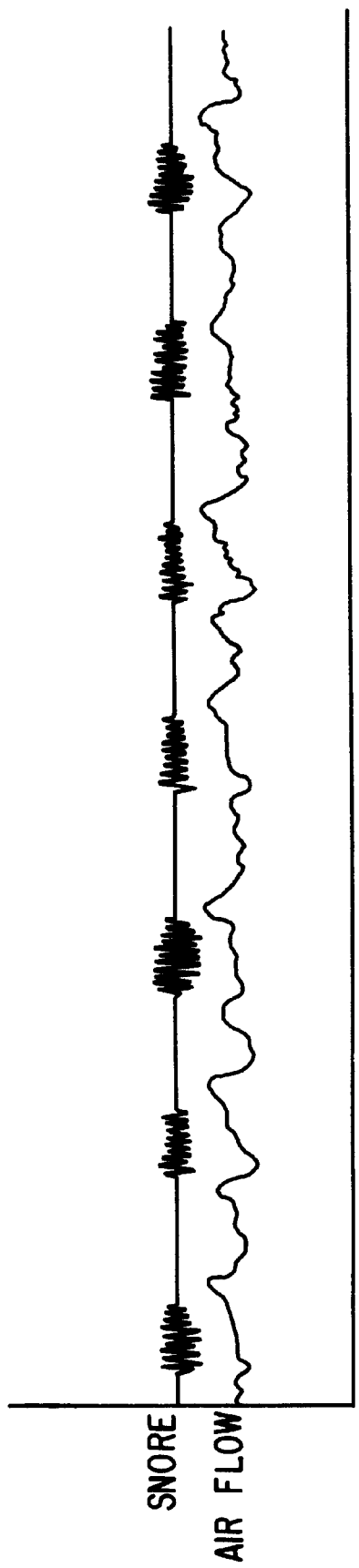

FIG. 4E are waveforms derived from an analyzer circuit manufactured and sold by Compumedics, an Australian company that manufactures and sells equipment to sleep laboratories and the like. Using the transducer of the present invention, the snoring pattern is readily detectable while the pyro signal labeled "air flow" clearly does not introduce false positives into the snoring channel, but instead, reflects air flow due to inhalation and exhalation. The observed difference in the waveforms of FIGS. 4A and 4C is due solely to the addition of a foam layer approximately $1/16^{th}$ of an inch thick covering the transducer film 12 over its entire surface.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A combination thermal and vibration sensor comprising:
   (a) a plastic film exhibiting pyroelectric and piezoelectric properties and having a predetermined shape configuration with first and second major surfaces;
   (b) a thin layer of conductive material deposited upon the first and second major surfaces;
   (c) first and second elongated conductive leads individually connected at a first end thereof to the layers of conductive material on the first and second major surfaces;
   (d) a layer of a material for changing the thermal mass of the sensor adhered to the layer of conductive material on at least one of the first and second major surfaces and coextensive with the predetermined shape configuration of said film.

2. The combination thermal and vibration sensor of claim 1 wherein said layer of material for changing the thermal mass is adhered to both of said first and second major surfaces.

3. The combination thermal and vibration sensor of claim 1 wherein the predetermined shape configuration is generally triangular.

4. The combination thermal and vibration sensor of claim 3 wherein three sides of the triangular shape configuration are arcuate defining at least two lobes.

5. The combination thermal and vibration sensor of claim 1 wherein the layer of conductive material is carbon.

6. The combination thermal and vibration sensor of claim 1 or claim 2 wherein the material for changing the thermal mass of the sensor is a layer of foamed plastic.

7. The combination thermal and vibration sensor of claim 6 wherein the thickness of the foam layer is in a range of from 0.001 to 0.150 inches.

8. The combination thermal and vibration sensor of claim 7 wherein the thickness of the foam layer is preferably about $1/16$ inches.

9. The combination thermal and vibration sensor as in claim 4 wherein the predetermined shape configuration includes first and second lobes adapted to be placed on a person's upper lip proximate the nares and a third lobe adapted to overlay a portion of the person's mouth.

10. The combination thermal and vibration sensor as in claim 1 wherein the layer of material for changing the thermal mass includes a pressure sensitive adhesive thereon for securing the sensor to an attachment surface; and a layer of peel-away release paper covering the adhesive prior to its application to an attachment surface.

11. The combination thermal and vibration sensor as in claim 10 wherein the layer of release paper includes a tab extending beyond an edge of said layer of material for changing the thermal mass of the sensor.

* * * * *